Figure 1:
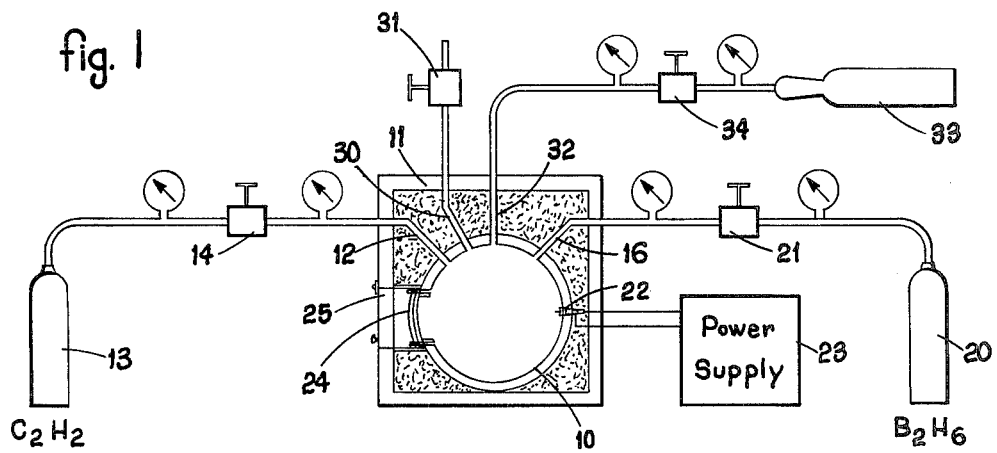

United States Patent [19]

Ditter et al.

[11] 4,017,587

[45] Apr. 12, 1977

[54] BORON CARBIDE

[75] Inventors: Jerome F. Ditter, Covina; Francis J. Gerhart, Temple City; Robert E. Williams, La Canada, all of Calif.

[73] Assignee: The United States of America as represented by the Secretary of the Navy, Washington, D.C.

[22] Filed: Apr. 26, 1971

[21] Appl. No.: 137,626

Related U.S. Application Data

[63] Continuation of Ser. No. 864,957, Oct. 3, 1969, abandoned, which is a continuation of Ser. No. 695,315, Dec. 27, 1967, abandoned.

[52] U.S. Cl. .............................................. 423/291
[51] Int. Cl.$^2$ ......................................... C01B 31/36
[58] Field of Search .......................... 423/291, 439

[56] References Cited

UNITED STATES PATENTS 3,379,647   4/1968   Smudski ............................. 23/204

OTHER PUBLICATIONS

Shapiro et al.: The Carboranes: $B_n C_2H_{n-2}$, II, The Two Isomers of $B_4C_2H_6$, J. Amer. Chem. Soc., 85, 3167 (1963).

Primary Examiner—Earl C. Thomas
Assistant Examiner—Wayne A. Langel
Attorney, Agent, or Firm—Richard S. Sciascia; Paul N. Critchlow

[57] ABSTRACT

This disclosure describes the process for producing an apparently amorphous porous boron carbide having a mean particle size less than 1 micron in diameter, effective pore sizes on the order of 30 Angstrom units, and surface areas on the order of 100 m$^2$/gr and greater. The process involves the gaseous phase reaction of acetylene ($C_2H_2$) with diborane ($B_2H_6$). The reaction is produced in a closed chamber initiated by an appropriate igniting device, such as a hot wire. This disclosure defines an optimum ratio of four parts diborane to one part acetylene and it describes the operating conditions under which the reaction occurs and the variation in physical properties and yield resulting from changes of ratio of the constituents. It also describes modification of the present batch process to a continuous production process. Typical uses for the material in its basic or altered form are described, such as a catalyst for gas-solid reactions, as a catalyst-supporting substrate for certain transition metals and other catalytic materials, as a gelling agent or grease thickener, as a thermal neutron absorber, either neat or in admixture with oils, etc., as a high temperature insulation material and as a fluidized bed heat exchange medium.

5 Claims, 2 Drawing Figures

BORON CARBIDE

This application is a continuation of copending and now-abandoned Ser. No. 864,957, filed Oct. 3, 1969 which was a continuation of abandoned Ser. No. 695,315, filed Dec. 27, 1967.

This invention relates to the production of submicron particles of refractory material and, more particularly, to an improved form of boron carbide and partially hydrogenated boron carbides and novel processes for their production.

FIELD OF THE INVENTION AND DESCRIPTION OF THE PRIOR ART

There is an ever expanding need for the production of sub-micron particles of refractory materials for use as temperature resistant additives to greases and as catalytic agents stable at elevated chemical reaction temperatures. While larger crystalline particles produced in electric furnaces have long been known and used as abrasive materials there has been a need for sub-micron boron carbide and for a process for producing the same which does not involve the use of elaborate electric furnaces which have been used in the production of boron carbide by the reaction. The traditional reaction of boric oxide, and coke to produce particulate boron carbide not only requires the use of electric furnaces, but it also tends to produce incomplete reactions, resulting in the presence of carbon and oxygen. The foregoing process also produces as its volatile product relatively valueless carbon monoxide.

SUMMARY OF THE INVENTION

In our investigation of carborane chemistry, that is, compounds of carbon, boron and hydrogen normally in the ratio of $C_2B_nH_{n+2}$, we attempted to produce new carboranes by the reaction of a number of hydrocarbon gases with boron hydrides. Contrary to expectations, the reaction of acetylene gas with diborane produced carboranes in only trace amounts and instead produced what has proved to be pure boron carbide or, in certain cases, hydrogenated boron carbide with a gas by-product of hydrogen. The reaction equation is as follows:

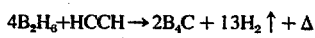

$$4B_2H_6 + HCCH \rightarrow 2B_4C + 13H_2 \uparrow + \Delta$$

Figure 2:
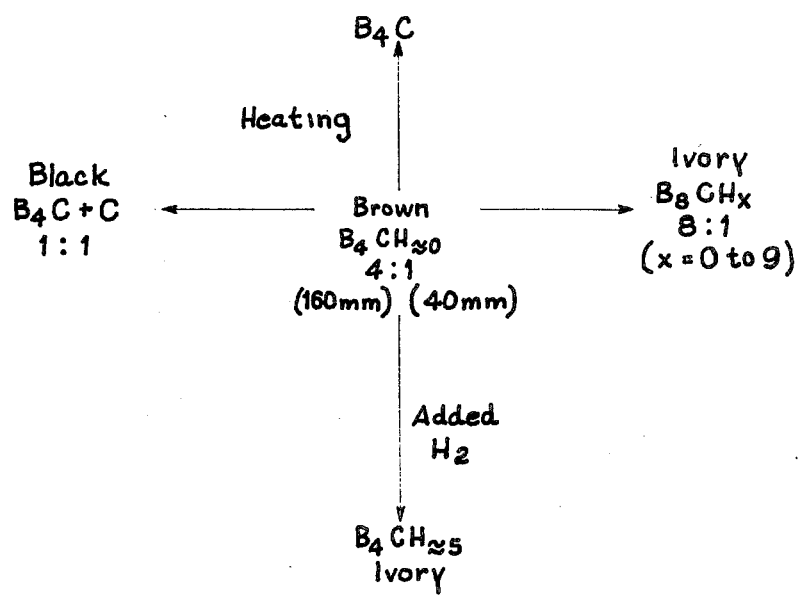

This invention may be more fully understood from the following detailed description and by reference to the drawing in which FIG. 1 is a simplified showing of the apparatus for producing the material of the invention, and FIG. 2 is a schematic representation of the variation in properties with changes in the process of this invention.

This reaction initiated by a hot wire was performed in both 34-liter and 300-liter closed chambers filled with diborane at a pressure of 160 millimeters and acetylene at 40 millimeters of mercury at room temperature. The exothermic nature of the reaction created a noticeable temperature rise, and the tank pressure increased to approximately 500 millimeters of mercury (corrected to room temperature).

The reaction gives a nearly stoichiometric yield of boron carbide which is light brown in color, of bulk density on the order of 0.015 grams per cc; it has no noticeable crystalline properties, either to visual inspection, to X-ray spectroscopy, or to electron microscopy at magnifications as great as 10,000 diameters. The particles exhibit a tendency to agglomerate and are noticeably porous with the mean pore size on the order of 30 Angstrom units and with a surface area in excess of 100 square meters per gram. At the 10,000 diameter magnification, the particles are reasonably uniform in size with reasonably regular surfaces. These latter properties are particularly significant in the use of boron carbide of this invention as a grease thickener or in other "fluidized bed" applications.

Chemical analysis of the product after centrifugation from water, using a common test for boron carbide, to wit, immersion in hot concentrated nitric acid, established that the material was essentially free from both elemental carbon and elemental boron. No chemical reactivity was detected when immersed in the nitric acid either at ambient temperature or when heated.

The reaction which produces the sub-micron boron carbide was carried out in a closed vessel, typified in FIG. 1 as a spherical chamber 10 in an insulated enclosure 11. The chamber 10 has an inlet port 12 from a source 13 of acetylene gas via valve 14. A similar inlet port 16 is used to introduce the diborane from supply 20 via valve 21. The reaction in chamber 10 is initiated by a glow plug or spark plug 22 in the chamber wall energized by a power supply 23. Access doors 24 and 25 to the chamber 10 and enclosure 11, respectively, allow the removal of the powder after completion of the reaction. Removal of the gaseous reaction product hydrogen is accomplished through exhaust port 30 by opening valve 31.

The chamber 10 configuration has a significant effect upon the reaction and the product, the effect diminishing with increasing volume. The reactant gases, when diborane is used, should be maintained at a relatively low temperature, i.e., less than 80° C, prior to reaction to avoid unwanted decomposition or side reactions, so the chamber is preferably maintained at room temperature prior to reaction. When reaction is initiated, the temperature rises because of the exothermic characteristic of the reaction. Because the cool walls of chamber 10 tend to quench the reaction, it is desirable that the reaction system be exposed to minimum quenching surfaces. For this reason, the spherical configuration is preferred. Where the reaction has been initiated in an elongated tube of relatively small diameter the solid product tends toward an ivory or yellow powder of bulk density greater than 0.015, indicative of the presence of greater amounts of hydrogen. The empirical formula in this latter case may be better represented as: $B_4CH_{\sim 5}$. Similar results occur when hydrogen is present prior to reaction.

In the foregoing equipment of FIG. 1, a flame is initiated at a point of ignition and the moving flame front then passes through the previously stationary chemical mixture of diborane and acetylene. In the wake of the flame front are left boron carbide and hydrogen.

A continuous production process can be developed in which the flame front is maintained stationary with respect to the container by moving the chemical reactants through the container (and flame) at a sufficiently high velocity. In this manner, the reactant gases move while the flame remains stationary, whereas in the former situation the gases are stationary and the flame front moves.

Although our prime interest is in the production of submicron boron carbide, $B_4C$, the addition of other vapors or gases to the chamber prior to initiation of the reaction may be desirable. For this reason, an additional inlet port 32 with its associated gas supply 33 and valve 34 is shown in FIG. 1. One gas which can be added is hydrogen, up to 12 to 15 parts hydrogen to one acetylene. At a ratio of 4:1:30 ($B_2H_6$, $C_2H_2$, $H_2$), the reaction is suppressed, but at lower hydrogen concentrations the reaction proceeds producing $B_4CH_X$ (where X varies between 0 and 5) which is useful where sub-micron particle size is not essential and where the attached hydrogen may serve to interact with, for example, appropriately reactive species to attach organic or inorganic substituents to the boron carbide surface. Examples include:

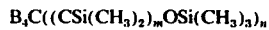

In the selection of reactant gases, we have produced reactions between acetylene and the following: Diborane, pentaborane-9, and decaborane-14. Diborane is preferred since it produces virtually a 90–100% yield of useful solid product (plus hydrogen). Pentaborane-9 or decaborane-14 when reacted with acetylene in ratios of 1.6:1 and 0.8:1 produce relatively pure boron carbide. These reactants provide smaller yield and larger particle sizes from diborane so at present are less favored. Other hydrocarbon gases such as methane, benzene, etc., which do not react sufficiently exothermally with diborane, are not considered useful in carrying out this invention.

Within the constraints of the diborane plus acetylene (and possibly hydrogen) system, the properties and consistency of the solid product may be varied by changing the ratio of the reactant gases as illustrated in FIG. 2. As indicated above, the preferred ratio for producing $B_4C$ is 4:1 diborane to acetylene. The effect of ratio change is illustrated in FIG. 2 of the drawing. As the ratio of diborane to acetylene is reduced, approaching 1:1, the resultant product approaches black is color, indicating excess carbon. As the ratio of diborane to acetylene is increased to 8:1, the color of the resultant product approaches ivory. At 20:1 (acetylene = 40mm) the mixture becomes increasingly difficult to ignite and at 30:1 the mixture did not ignite by a spark or hot wire, at least not at ambient room temperatures. The 8:1 product is rich in hydrogen, the empirical formula approximating $B_8CH_X$, where X has a value on the order of nine. Addition of hydrogen also produces ivory colored products whose empirical compositions may be bracketed by the formulas ($B_4CH_{\approx 0}$ to $B_4CH_{\approx 5}$). Heating the various compositions to temperatures in excess of 900° C drives off hydrogen, to produce $B_4C$.

The use of sub-micron boron carbide are numerous. First, it has been demonstrated as a useful thickening agent in lubricants. The function of a thickening agent in a lubricant is to give a low viscosity oil base sufficient body so as to be retained in a journal while under dynamic load conditions. Powders are frequently used as thickeners for this purpose, and particle size, shape and density are known to be dominant factors in controlling rheological characteristics of greases thickened with inorganic additives. Generally, the less the amount of additive required to bring the grease to a desired consistency, the better will be its overall lubricating characteristics because the additive itself usually does not possess as good lubricating properties as the oil. In a high speed bearing test with a grease thickened by boron carbide powder in accordance with our invention, only about 7% by weight of powder was required to bring a fluorocarbon base oil to a desired consistency compared with values of 20–40% by weight for other organic thickening agents. The fine state of division of the sub-micron boron carbide powder almost certainly was a major factor responsible for the small percent required to thicken the grease.

The thickening properties of the sub-micron boron carbide powder also enable it to be utilized as a general gelling agent for liquidus materials and as an inert filler for compounding polymers as well. In the latter case, the sub-micron boron carbide could be used to impart chemical resistance to a polymer, such as enhanced oxidation resistance to a silicone rubber polymer. Other functions it might serve as a polymer filler include increasing hardness and improving thermal insulation properties. It is particularly useful as a thermal neutron absorber.

Boron, specifically the $^{10}$B-isotope, has a large capture cross section for slow neutrons. Our sub-micron boron carbide powder, which can be prepared either in a natural isotopic composition (approximately 20% $^{10}$B-isotope and 80% $^{11}$B-isotope) or in an isotopically enriched state (for example, 96% $^{10}$B-isotope and 4% $^{11}$B-isotope) can therefore function as an effective thermal neutron absorber. It would be particularly useful in this respect as shielding around a nuclear reactor since, because of its fine state of division, it can be suspended in a liquid or can be pumped as a fluidized solid and could serve simultaneously as a thermal neutron absorber and as a heat exchange medium. Another important factor is the high concentration of boron in the molecular composition of boron carbide (empirically $B_4C$) so that approximately 80% of the material on a molar basis is boron.

The high surface area ($\approx 100$ square meters per gram) of the sub-micron boron carbide solid makes it a candidate as a catalyst for reactions of gases on solid surfaces. It would be particularly effective if allowed to flow as a fluidized solid countercurrent to a moving gas stream so that maximum surface is exposed to the gases. Because of the low bulk density of our boron carbide powder, counterflow of the material may not be necessary to achieve intimate contact with incoming reactant gases. Even low flow rates of gases tend to continually churn and suspend the particles. Furthermore, by allowing the original reaction between acetylene and the borane to take place in the presence of the appropriate volatile metallo-organic compound(s) the powder could be doped with a desired metal or metallo-organic substituent to tailor it for a particular type of reaction.

The foregoing is a description of one or more embodiments of our invention. It is recognized that one skilled in the art can devise variations from the specific forms in which our invention is illustrated. In accordance with the Patent Laws of the United States, the rights granted thereunder are not limited to the specific embodiments illustrated, but rather by the scope of the following claims and their equivalents.

We claim:

1. A process of producing a boron carbide powder comprising the steps of:
providing a gaseous mixture of diborane and acetylene at a temperature less than 80° C to inhibit undesired side reactions and decomposition of the gases;

igniting the relatively low temperature gaseous mixture for producing a flame front;

promoting a relative movement between said flame front and said gaseous mixture for consuming the mixture in a flame reaction whereby said boron carbide powder is produced; and recovering a reaction product of boron carbide powder.

2. The process of claim 1 wherein the ratio of gaseous mixture of diborane and acetylene is in the range of 1:1 to 20:1.

3. The process of claim 1 wherein the ratio of the gaseous mixture of diborane and acetylene is about 4:1.

4. The process of claim 1 wherein the reactant gases comprise diborane, acetylene and hydrogen.

5. A boron carbide powder of a porous nature with a surface area in excess of 100 $m^2$ per gram and with a mean pore size of about 30 Angstrom units and a mean particle diameter of less than one micron, said powder being produced by a gaseous phase reaction of a boron hydride and acetylene and being amorphous to the extent that it has no apparent crystalline properties under X-ray spectroscopy and electron microscopy at magnifications up to 10,000 diameters.

* * * * *